US009335155B2

(12) United States Patent
Uchida

(10) Patent No.: US 9,335,155 B2
(45) Date of Patent: May 10, 2016

(54) IMAGING APPARATUS, IMAGE PROCESSING APPARATUS, AND IMAGE PROCESSING METHOD

(71) Applicant: CANON KABUSHIKI KAISHA, Tokyo (JP)

(72) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/011,363

(22) Filed: Aug. 27, 2013

(65) Prior Publication Data
US 2014/0063508 A1    Mar. 6, 2014

(30) Foreign Application Priority Data
Aug. 30, 2012    (JP) .................................. 2012-190002

(51) Int. Cl.
G01B 9/02    (2006.01)
A61B 3/10    (2006.01)

(52) U.S. Cl.
CPC ............ G01B 9/02091 (2013.01); A61B 3/102 (2013.01); G01B 9/0203 (2013.01); G01B 9/02044 (2013.01); G01B 9/02085 (2013.01)

(58) Field of Classification Search
CPC ...... G01B 9/02; A61B 5/0066; A61B 5/6852; A61B 5/0073; G01N 21/4795
USPC ........................................................ 356/479
See application file for complete search history.

(56) References Cited

U.S. PATENT DOCUMENTS

| 8,180,134 | B2 * | 5/2012 | Wang ..................... A61B 3/102 382/130 |
| 8,711,366 | B2 * | 4/2014 | Everett .................. A61B 3/102 356/497 |
| 8,781,214 | B2 | 7/2014 | Davis et al. |
| 2006/0228011 | A1 * | 10/2006 | Everett .................. A61B 3/113 382/128 |
| 2007/0291277 | A1 * | 12/2007 | Everett .................. A61B 3/102 356/497 |
| 2010/0219819 | A1 * | 9/2010 | Kimura et al. ................ 324/244 |
| 2011/0228222 | A1 * | 9/2011 | Kobayashi .................... 351/206 |
| 2012/0007863 | A1 * | 1/2012 | Endo et al. .................... 345/419 |
| 2012/0328156 | A1 * | 12/2012 | Nakano ................ G06T 7/0083 382/103 |

FOREIGN PATENT DOCUMENTS

| CN | 102264282 A | 11/2011 |
| CN | 102438502 A | 5/2012 |
| CN | 102458221 A | 5/2012 |
| JP | 201136431 A | 2/2011 |
| WO | 2010134641 A1 | 11/2010 |
| WO | 2010140601 A1 | 12/2010 |
| WO | 2011121959 A2 | 10/2011 |
| WO | 2011121962 A1 | 10/2011 |

* cited by examiner

Primary Examiner — Tarifur Chowdhury
Assistant Examiner — MD Rahman
(74) Attorney, Agent, or Firm — Canon USA Inc., IP Division

(57) ABSTRACT

An imaging apparatus includes a reconstruction unit configured to reconstruct a tomographic image of a predetermined range of a measurement object based on interference light produced by interference between returning light of measurement light from the measurement object and reference light, and a generation unit configured to, for each pixel value row in a depth direction of the tomographic image, generate a two-dimensional image based on a pixel value selected in order of magnitude of the pixel values.

24 Claims, 11 Drawing Sheets

IMAGING APPARATUS, IMAGE PROCESSING APPARATUS, AND IMAGE PROCESSING METHOD

BACKGROUND OF THE INVENTION

1. Field of the Invention

The present invention relates to a technique for obtaining a two-dimensional image from information about a tomographic image obtained based on light interference.

2. Description of the Related Art

Currently, imaging apparatuses that employ optical coherence tomography (OCT) in which multi wavelength interference is utilized are being used in more and more fields of application on the human body to obtain, for example, information about internal organs with an endoscope, and information about the retina with an ophthalmologic apparatus. An imaging apparatus that is applied to the eye is becoming an essential apparatus for specialist retina out-patient clinics as an ophthalmologic device.

Such an imaging apparatus can irradiate measurement light, which is low-coherence light, on a sample and measure the backscattered light from that sample using an interference system. Further, such an imaging apparatus is widely used in the ophthalmologic diagnosis of the retina because, when applied to an eye, a high resolution tomographic image of a subject's eye can be captured by scanning measurement light over the subject's eye.

Japanese Patent Application Laid-Open No. 2011-36431 discusses a configuration capable of acquiring a surface image of an imaging target, such as a fundus surface, to confirm the imaging range of a tomographic image.

On the other hand, there is a need to more accurately confirm the position of a cross-section on the fundus surface (i.e., imaging target).

In response thereto, a technique is known for generating a pseudo two-dimensional image, from a plurality of tomographic images, in which the fundus is viewed from the front (hereinafter referred to as a "two-dimensional image"). In this technique, pixel values of a predetermined range in the depth direction obtained by one A scan are calculated. Then, by obtaining these calculated values for all the A scans, a two-dimensional image of the retina can be obtained from only tomographic images.

However, in the above-described technique, since the two-dimensional image is obtained by calculating the pixel values of a predetermined range obtained by an A scan in the depth direction of the retina, unnecessary information, such as a noise component, that is included in the depth direction information is also calculated. Consequently, the amount of effective information about an intensity image is relatively smaller, so that the quality of the intensity image may deteriorate.

SUMMARY OF THE INVENTION

The present invention is directed to an imaging apparatus imaging apparatus, an image processing apparatus, and an image processing method capable of generating a two-dimensional image without causing image quality thereof to deteriorate.

According to an aspect of the present invention, an imaging apparatus includes a scanning unit configured to scan a measurement object with measurement light, a reconstruction unit configured to reconstruct a tomographic image in a predetermined range of the measurement object based on interference light produced by interference between returning light of the measurement light from the measurement object and reference light, and a generation unit configured to, for each pixel value row in a depth direction of the tomographic image, generate a two-dimensional image based on a pixel value selected in order of magnitude of the pixel values.

Further features of the present invention will become apparent from the following detailed description of exemplary embodiments with reference to the attached drawings.

DESCRIPTION OF THE EMBODIMENTS

Figure 1:
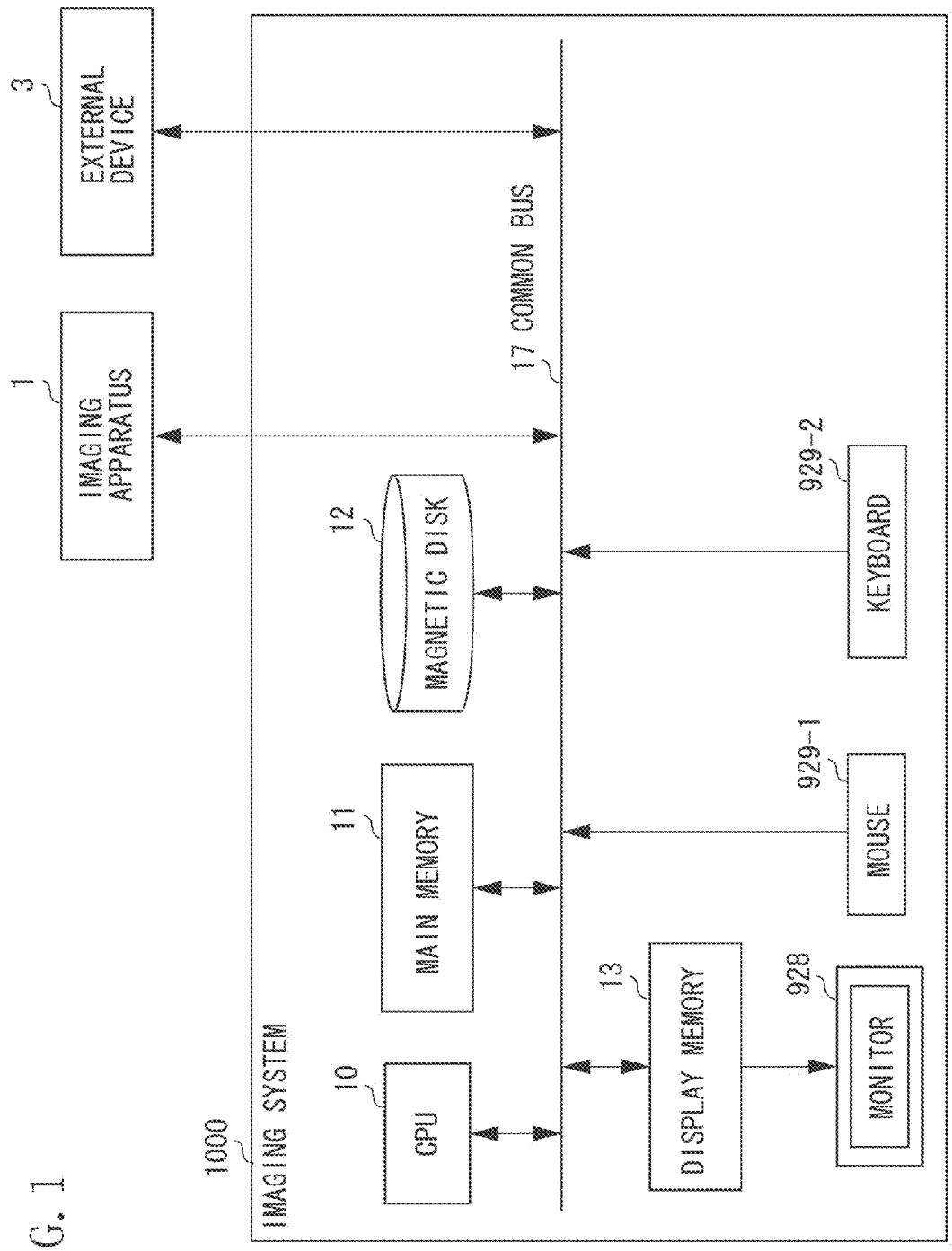
FIG. 1 is a block diagram illustrating a configuration of an imaging system.

FIG. 1 illustrates a configuration example of an imaging system 1000 including an image processing apparatus 100 according to a first exemplary embodiment and an imaging apparatus 1 connected to the image processing apparatus 100. The image processing apparatus 100 is configured of a central processing unit (CPU) 10, a main memory 11, a magnetic disk 12, and a display memory 13. Further, the imaging system 1000 includes a monitor 928, a mouse 929-1, and a keyboard 929-2.

The CPU 10 mainly controls the operation of each constituent element of the image processing apparatus 100. The main memory 11 stores control programs executed by the CPU 10, and provides a work area during program execution by the CPU 10. The magnetic disk 12 stores an operating system (OS), device drivers for peripheral devices, and various application software including programs for performing the below-described deformation estimation processing. The display memory 13 temporarily stores display data for the monitor 928. The monitor 928, which is a cathode ray tube (CRT) monitor or a liquid crystal monitor, displays an image based on data from the display memory 13. The mouse 929-1 and the keyboard 929-2 are used by the user to perform pointing input and to input characters, respectively. Each of the above-described constituent elements are communicably connected to each other via a common bus 17.

The image processing apparatus 100, which is connected to the imaging apparatus 1 via a local area network (LAN), can acquire image data from the imaging apparatus 1. However, the exemplary embodiments of the present invention are not limited to this. For example, the connection between these devices can also be performed via some other interface, such as a universal serial bus (USB) or Institute of Electrical and Electronics Engineers (IEEE) 1394. Further, the necessary data may also be read via a LAN or the like from an external device 3, such as a data server, that manages this data. In addition, a storage device, such as a floppy disk drive (FDD), a compact disc-rewritable (CD-RW) drive, a magneto-optic disc (MO) drive, and a ZIP drive, may be connected to the image processing apparatus 100, and the necessary data may be read from that drive.

Figure 2:
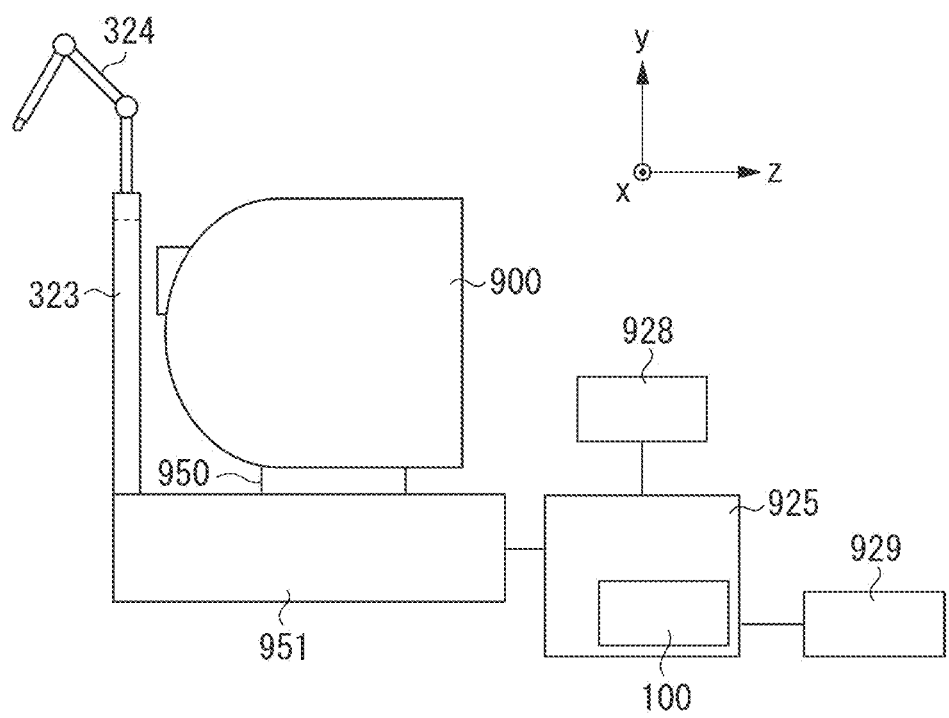
FIG. 2 is a side view of an imaging system.

The imaging system illustrated in FIG. 2 includes an optical head 900, which is a measurement light optical system for capturing an anterior eye image, a fundus surface image, and a tomographic image, a stage section 950, which is a movement unit that can move the optical head in the XYZ directions in FIG. 2 using a (not-illustrated) motor, and a base section 951 that houses a below-described spectroscope.

A personal computer 925, which also acts as a control unit for the stage section, includes the image processing apparatus 100. A chin rest 323 helps to fix the subject's eye (eye to be examined) by fixing the subject's chin and brow. An external fixation target 324 is used to visually fix the subject's eye. Further, the image processing apparatus 100 may also be included in the optical head 900 or the stage section 950. In this case, the imaging apparatus 1 and the image processing apparatus 100 are integrally configured as an imaging apparatus.

Figure 3:
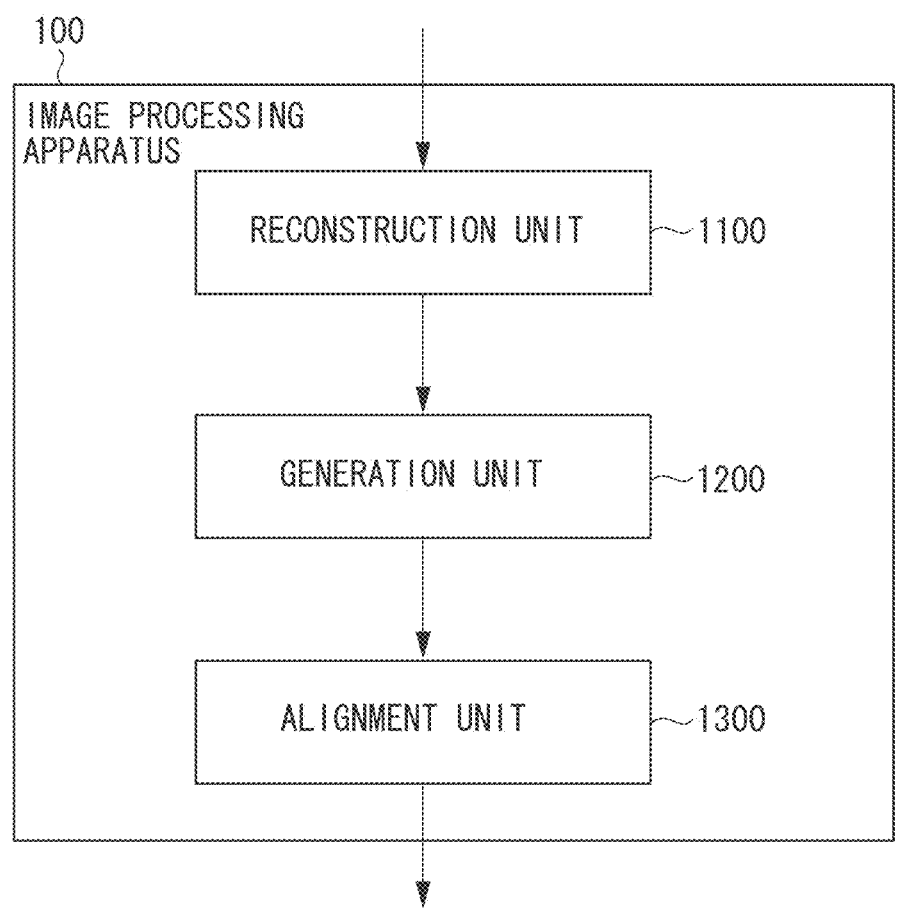
FIG. 3 is a block diagram illustrating a configuration of an image processing apparatus according to a first exemplary embodiment.

FIG. 3 is a block diagram illustrating a function configuration of the image processing apparatus 100. A reconstruction unit 1100 obtains a tomographic image of a predetermined range of a measurement object based on interference light produced by interference between returning light of measurement light from the measurement object and reference light. An output value from a sensor is subjected to frequency conversion and fast Fourier transformation (FFT) processing, and is reconstructed as a tomographic image (an A scan image) in the depth direction at one point on the fundus of the subject's eye.

Further, a generation unit 1200 generates a two-dimensional image by selecting for each pixel value row a predetermined pixel from each pixel value row in the depth direction of the tomographic image obtained by the reconstruction unit 1100.

An alignment unit 1300 for aligning the two-dimensional image obtained by the generation unit 1200 with a surface image and the tomographic image of the measurement object. The alignment unit 1300 also has a function of aligning the surface image of the measurement object with the two-dimensional image generated by the generation unit 1200 by using template matching. This template matching is processing that superimposes the images so as to overlap characteristic points, such as a blood vessel branch point, on each image. Further, this template processing also includes processing for aligning the two-dimensional image generated by the generation unit 1200 and the surface image of the measurement object so that a correlation value obtained by evaluating the level of overlap among the images is at a maximum.

Figure 4:
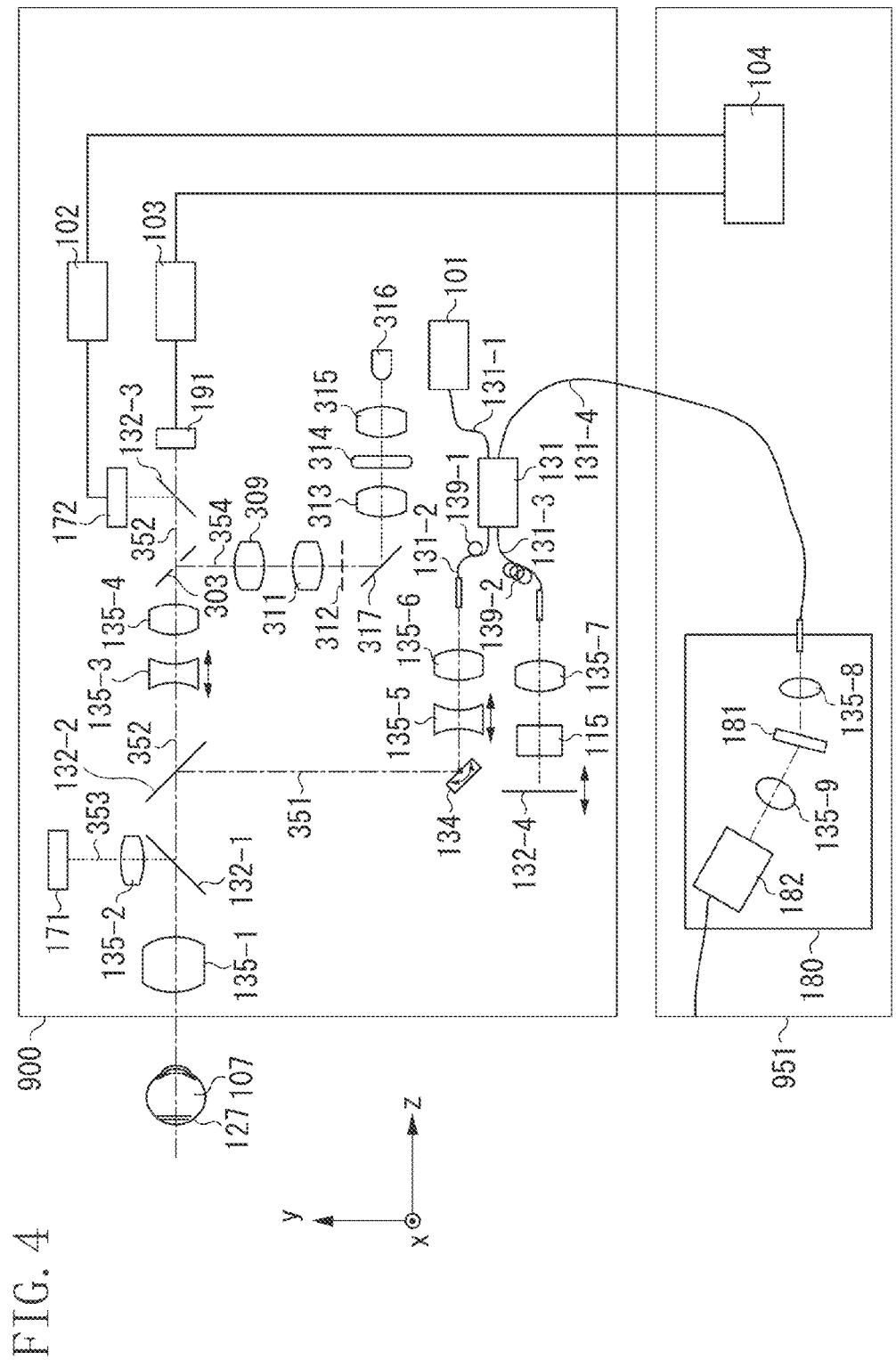
FIG. 4 is a configuration diagram of an optical system in an imaging apparatus.

FIG. 4 illustrates the configuration of the measurement light optical system and the spectroscope in the imaging apparatus 1. First, the internal configuration of the optical head 900 will be described.

An objective lens 135-1 is arranged facing a subject's eye 107 as an example of the measurement object. On that optical axis, light is split by a first dichroic mirror 132-1 and a second dichroic mirror 132-2 for each wavelength band into a light path 351 for an OCT optical system, a light path 352 for fundus observation and for a fixation lamp, and a light path 353 for anterior eye observation.

A lens 135-3 is driven by a (not illustrated) motor for focus adjustment of a fixation target 191 and a fundus observation charge-coupled device (CCD) 172.

A perforated mirror 303, which is arranged between a lens 135-4 and a third dichroic mirror 132-3, splits the light path 352 into the light path 352 and a light path 354.

The light path 354 forms an illumination optical system that illuminates the fundus of the subject's eye 107. A light-emitting diode (LED) light source 316, which is an illumination light source for fundus observation used for alignment of the subject's eye 107, and a flash tube 314, which is used to capture an image of the fundus of the subject's eye 107, are arranged on the light path 354.

The optical head 900 also includes lenses 309 and 311, condenser lenses 313 and 315, and a mirror 317. The illumination light from the LED light source 316 and the flash tube 314 is formed into a ring-shaped light beam by a ring slit 312. This ring-shaped light beam is reflected by the perforated mirror 303, and illuminates a fundus 127 of the subject's eye 107. The LED light source 316 is a light source that has a center wavelength of around 780 nm.

After the perforated mirror 303 on the light path 352, light is split in the same manner as described above by the third dichroic mirror 132-3 for each wavelength band into a light path to the fundus observation CCD 172 and the fixation target.

The CCD 172, which is connected to a CCD control unit 102, is sensitive to the center wavelength of the LED light source 316, which is illumination light for fundus observation, specifically, around 780 nm. On the other hand, the fixation target 191, which is connected to a fixation target control unit 103, generates visible light to help with visual fixation of the subject.

The CCD control unit 102 and the fixation target control unit 103 are connected to a calculation unit 104. Data is input to and output from the personal computer 925 via the calculation unit 104.

The optical head 900 also includes a lens 135-2, and an infrared CCD 171 for anterior eye observation. This CCD 171 is sensitive to the wavelength of (not illustrated) illumination light for anterior eye observation, specifically, around 970 nm. Further, an image splitting prism (not illustrated) is arranged on the light path 353, which enables the distance in the Z direction of the optical head unit 900 from the subject's eye 107 to be detected as a split image in the anterior eye observation image.

As described above, the light path 351 forms the OCT optical system for capturing a tomographic image of the retina of the subject's eye 107. More specifically, the light path 351 is for obtaining an interference signal for forming a tomographic image. An XYZ scanner 134 scans the fundus with light. Although the XYZ scanner 134 is illustrated as a single mirror, the XYZ scanner 134 scans in two directions, the X direction and the Y direction. A lens 135-5 is driven by a motor (not illustrated) for adjusting the focus on the fundus 100 of light from a light source 101 that irradiates light from a fiber 131-1 which is connected to an optical coupler 131. Based on this focus adjustment, the light from the fundus 127 is simultaneously incident on a tip of a fiber 131-2 to form a spot-like image.

Next, the light path from the light source 101 and the configuration of a reference optical system and a spectroscope will be described.

The optical head 900 includes the light source 101, a mirror 132-4, glass 115 for scattered light compensation, the above-described optical coupler 131, single-mode optical fibers 131-1 to 131-4 that are integrally connected to the optical coupler, a lens 135-7, and a spectroscope 180. These parts configure a Michelson interference system. The light irradiated from the light source 101 passes through the optical coupler 131 via the optical fiber 131-1, and is split into measurement light on the optical fiber 131-2 side and reference light on an optical fiber 131-3 side.

The measurement light passes through the above-described OCT optical system, is irradiated on the fundus of the subject's eye 107, which is the observation target, and reaches the optical coupler 131 via the same light path due to reflection and scattering by the retina.

On the other hand, the reference light reaches and is reflected by the mirror 132-4 via the optical fiber 131-3, the lens 135-7, and the scattered light compensation glass 115, which is inserted to match the scattering of the reference light with the measurement light. The reference light returns along the same light path, and reaches the optical coupler 131.

At the optical coupler 131, the measurement light and the reference light are combined to form interference light. This interference is produced when the light wavelength of the measurement light and the light wavelength of the reference light are nearly the same. The mirror 132-4 is adjustably held in the optical axis direction by a motor (not illustrated) and a drive mechanism, so that the light wavelength of the reference light can be made to match the light wavelength of the measurement light that changes based on the subject's eye 107. The interference light is guided to the spectroscope 180 via the optical fiber 131-4.

A measurement light side polarization adjustment unit 139-1 is arranged in an optical fiber 131-2. A reference light side polarization adjustment unit 139-2 is arranged in the optical fiber 131-3. These polarization adjustment units include several portions formed by winding the optical fiber into a loop shape. These polarization adjustment units can adjust and match the respective polarization states of the measurement light and the reference light by turning the loop shape portions around the longitudinal direction of the fiber so as to twist the fiber. In the imaging apparatus 1, the polarization states of the measurement light and the reference light are adjusted and fixed in advance.

The spectroscope 180 is configured of lenses 135-8 and 135-9, a diffraction grating 181, and a line sensor 182.

The interference light irradiated from the optical fiber 131-4 passes through the lens 135-8 to be substantially parallel. The interference light is then split by the diffraction grating 181, and is focused on the line sensor 182 by the lens 135-3. The output from the line sensor 182 is input into the personal computer 925.

Next, the light source 101 will be described in detail. The light source 101 is a super luminescent diode (SLD), which is a representative low-coherence light source. The center wavelength is 855 nm, and the wavelength band width is about 100 nm. Since the band width affects the resolution in the optical axis direction of the obtained tomographic image, it is an important parameter. Further, although in the present exemplary embodiment, an SLD was selected as the type of light source, as long as low-coherence light can be emitted, some other light source may be used, such as amplified spontaneous emission (ASE). Considering that the center wavelength is used to measure an eye, near infrared light is suitable. Further, since the center wavelength affects the resolution in the sideways direction of the obtained tomographic image, it is desirable for the wavelength to be as short as possible. Based on both of these reasons, a center wavelength of 855 nm was selected.

In the present exemplary embodiment, although a Michelson interferometer was used as an interferometer, a Mach-Zehnder interferometer may also be used. Based on the difference in the quantity of light between the measurement light and the reference light, it is desirable to use a Mach-Zehnder interferometer when the difference in the quantity of light is large and a Michelson interference when the difference in the quantity of light is comparatively small.

Next, a method for capturing an image of the subject's eye using the present imaging apparatus will be described.

First, the operator makes the patient sit in front of the imaging apparatus according to the present exemplary embodiment, and starts capturing a surface image of the subject's eye fundus. Light irradiated from the light source 316 is formed into a ring-shaped light beam by the ring slit 312, reflected by the perforated mirror 303, to irradiate the fundus 127 of the subject's eye 107. A reflection light beam from the fundus 127 passes through the perforated mirror 303, and focuses on the CCD 172. The reflection light from the fundus 127 that was focused on the CCD 172 is turned into an image of the surface of the fundus by the CCD control unit 102, and the obtained image is transmitted to the image processing apparatus 100.

Next, the imaging apparatus 1 captures a tomographic image of a desired site on the fundus of the subject's eye 107 by controlling the XYZ scanner 134.

Light irradiated from the light source 101 passes through the optical fiber 131-1, and is split by the optical coupler 131 into measurement light heading toward the subject's eye and reference light heading toward a reference mirror 132-4.

The measurement light heading toward the subject's eye passes through the optical fiber 131-2, is irradiated from the tip of the fiber, and is incident on the XYZ scanner 134. The measurement light polarized by the XYZ scanner 134 passes through the optical system 135-1 and illuminates the subject's eye fundus 127. Then, the reflection light reflected by the subject's eye follows the reverse path to return to the optical coupler 131.

On the other hand, the reference light heading toward the reference mirror passes through the optical fiber 131-3, is irradiated from the tip of the fiber, passes through a collimated optical system 135-7 and the scattered light compensation optical system 115, and arrives at the reference mirror 132-4. The reference light reflected by the reference mirror 132-4 then follows the reverse path to return to the optical coupler 131.

The measurement light and the reference light that have returned to the optical coupler 131 interfere with each other. The produced interference light is incident to the optical fiber 131-4, is turned into substantially parallel light by the optical system 135-8, and is incident on the diffraction grating 181. The interference light incident on the diffraction grating 181 is focused on the line sensor 182 by an imaging lens 135-9, so that an interference signal at one point on the subject's eye fundus can be obtained.

An output value is output to the image processing apparatus 100 as an image signal including interference information obtained from a plurality of elements of the line sensor 182. Although in the example described referring to FIG. 4, the surface image of the fundus is obtained at one time with the light irradiated from the flash tube 314, the surface image of the fundus can also be obtained by scanning laser ophthalmoscopy (SLO) in which light irradiated by the SLD light source is scanned.

Figure 5:
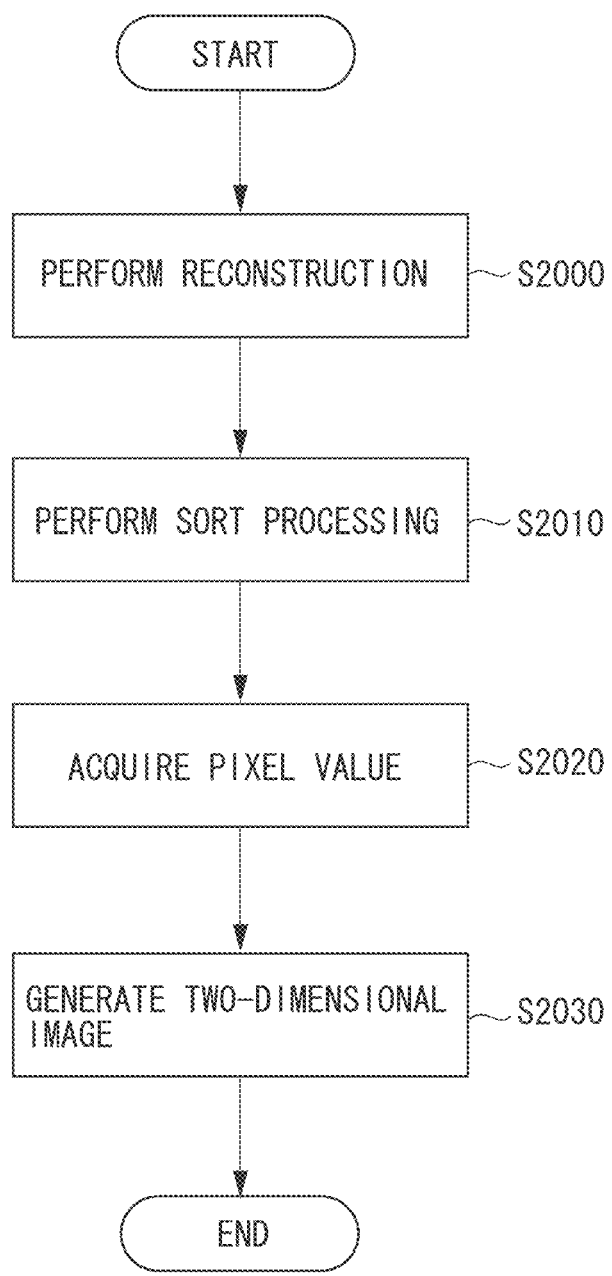
FIG. 5 is a flowchart illustrating a flow of processing performed by an image processing apparatus according to a first exemplary embodiment.

Next, the flow of an image processing method performed by the image processing apparatus 100 will be described with reference to FIG. 5.

After the tomographic information at one point on the subject's eye fundus has been acquired, the imaging apparatus 1 drives the XYZ scanner 134 that acts as a scanning unit in the X direction to produce interference light at another point on the subject's eye fundus. This interference light at another point passes through the line sensor 182 and is input into the reconstruction unit 1100. The reconstruction unit 1100 forms a tomographic image (an A scan image) in the depth direction at this another point on the subject's eye fundus. The coordinates of the A scan image are associated with the position of the XYZ scanner 134 that captured the interference signal of the A scan, and stored.

In step S2000, the reconstruction unit 1100 reconstructs one tomographic image (B scan image) in the horizontal direction of the subject's eye fundus by consecutively driving the XYZ scanner 134 in the X direction.

Then, the reconstruction unit 1100 reconstructs a horizontal tomographic image (B scan image) at another position in the Y direction on the subject's eye fundus by, after driving the XYZ scanner 134 a predetermined amount in the Y direction, performing the above-described scanning again in the X direction. By repeating this Y direction driving of the XYZ scanner 134, a plurality of tomographic images can be formed that cover a predetermined range of the fundus 127. In the imaging apparatus 1, the reconstruction unit 1100 forms 128 tomographic images by repeating the formation of B scan images while driving a predetermined small amount of 128 times in the Y direction. Further, the reconstruction unit 1100 reconstructs (forms) a three-dimensional tomographic image from the 128 tomographic images.

Next, the generation unit 1200 generated a two-dimensional image of the retina from the tomographic image generated by the reconstruction unit 1100.

Figure 6:
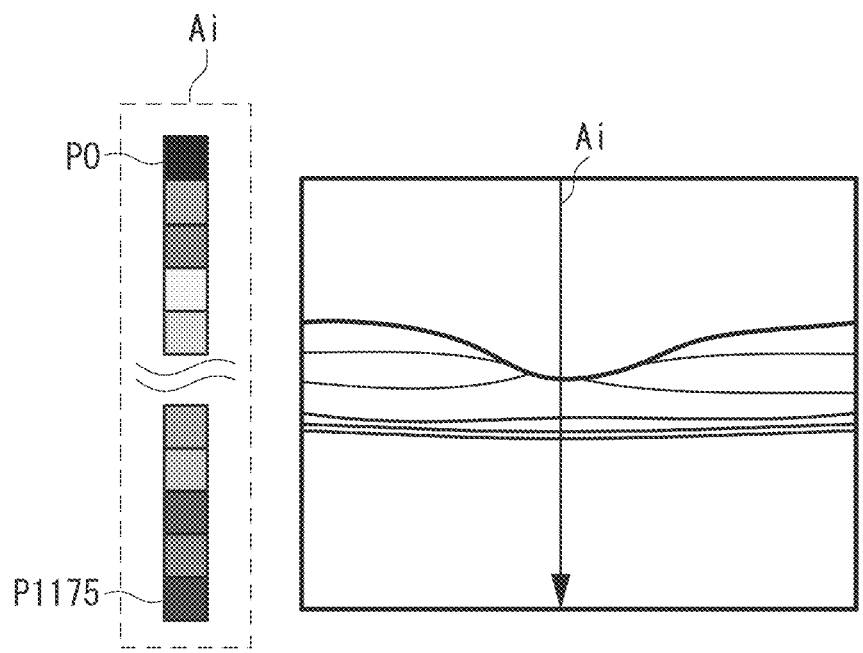
FIG. 6 illustrates a pixel value row of an A scan image.

As described above, an A scan image is a tomographic image in the depth direction at one point on the subject's eye fundus, and as illustrated in FIG. 6, is formed from a plurality of luminance information in the depth direction.

The two-dimensional tomographic image in FIG. 6 is a collection of the A scan images. This two-dimensional tomographic image may be a B scan image or may be a cross-section of a three-dimensionally reconstructed tomographic image.

For example, in the imaging apparatus 1, using a line sensor 182 that includes 1,176 pixels, an A scan image Ai that has been subjected to FFT forms a pixel value row from 1,176 pixel values. In this case, P0 represents a pixel value as luminance information about the shallowest section in the depth direction based on color density, and P1175 represents a pixel value as luminance information about the deepest section in the depth direction.

The imaging apparatus obtains a pixel value at one point on the subject's eye fundus as a representative intensity signal by selectively extracting one piece of luminance information from this plurality of luminance information. In other words, the imaging apparatus selects one pixel value from the 1,176 pixel values obtained from the A scan. The generation unit 1200 may be configured to generate a two-dimensional image by processing the reconstructed tomographic image acquired by a (not illustrated) acquisition unit 2000 from the external device 3. In this case, the generation unit receives a direct input from the acquisition unit 2000 that has not passed through the reconstruction unit 1100.

Figure 7:
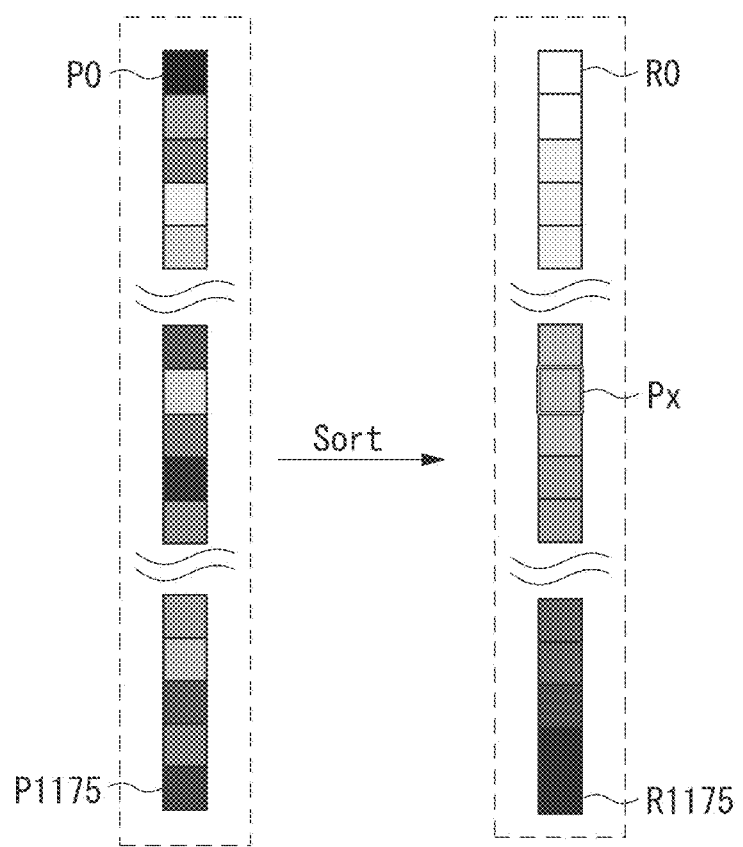
FIG. 7 illustrates pixel value sorting.

In step S2010, the generation unit 1200 sorts the luminance information about the tomographic image corresponding to each A scan as illustrated in FIG. 7 in order of larger luminance. More specifically, the generation unit 1200 ranks the pixel values based on the magnitude of the pixel values in each of the rows having 1,176 pixel values, and sorts the pixel values based on that ranking.

R0 is the pixel that has the brightest luminance information as a pixel value, and R1175 is the pixel that has the darkest luminance information as a pixel value. Since luminance indicates the interference intensity, the pixel values also correspond to interference intensity.

Further, the generation unit 1200 selects a pixel Rx of a predetermined ranking. This pixel of a predetermined ranking is a pixel positioned x places from the top after the pixel values were sorted in order of larger luminance information. Since the retina tomographic image is formed mostly from dark pixels, it is desirable for x to be a pixel positioned in the top half of all the pixels. For example, if an A scan image formed from pixel value rows having a total of 1,176 pixels is used, the 118-th pixel from the top, which is in the top 10%, maybe selected as the pixel Rx of a predetermined ranking. As a result, the pixel value is selected that corresponds to the pixel Rx with the predetermined ranking.

In step S2020, the generation unit 1200 determines the luminance information about the pixel Rx with the predetermined ranking as the intensity information for that A scan. Further, by determining the intensity information for all of the A scan images, a pixel value can be obtained as the intensity information at each point corresponding to the illumination position of the scanned measurement light of the fundus 127. In this case, the pixel values are stored in a memory 3000 (not illustrated) as intensity information corresponding to the two-dimensional coordinates of each illumination position of the measurement light scanned on the fundus 127. Then, in step S2030, a two-dimensional image I of the retina as illustrated in FIG. 7 can be obtained by generating a two-dimensional image (sometimes referred to as "intensity image" or "intensity") based on the pixel value corresponding to the coordinates stored in the memory 3000.

An example has been described above in which a two-dimensional image is generated by the generation unit 1200 after all of the data had been reconstructed by the reconstruction unit 1100. However, a tomographic image reconstructed for each A scan may be successively transmitted to the generation unit 1200, or a tomographic image reconstructed for each B scan may be successively transmitted to the generation unit 1200.

This two-dimensional image, which is an image analogous to the surface image of the fundus obtained by the CCD 172, or a fundus image obtained by another fundus camera or SLO can virtually visualize the fundus surface. Further, since only effective information is selectively acquired from the plurality of luminance information, a preferable two-dimensional image can be obtained that is not affected by the noise component included in the A scan images or a dark area having a low interference intensity.

Figure 8:
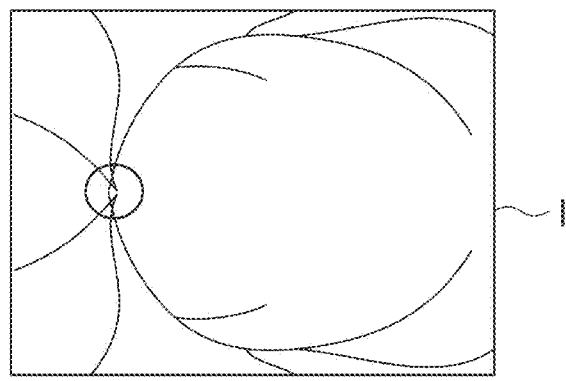
FIG. 8 illustrates a two-dimensional image of a retina.
Figure 9:
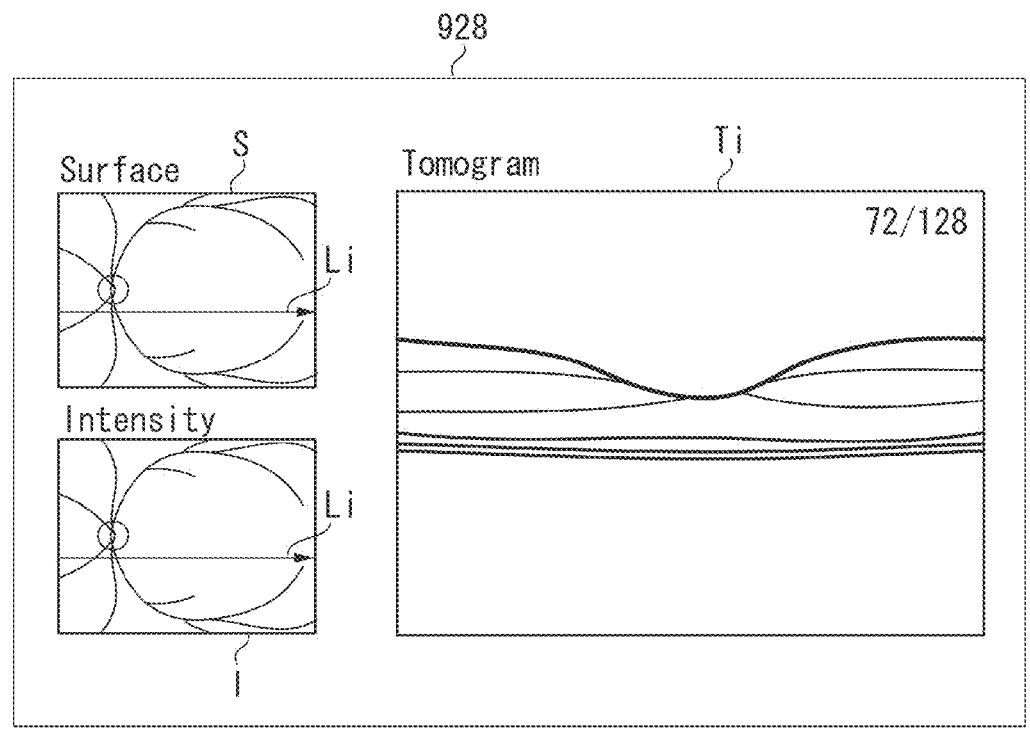
FIG. 9 illustrates a display example of a tomographic image and a two-dimensional image.

Next, the alignment unit 1300 aligns the surface image, the tomographic image, and the two-dimensional image of the fundus generated by the imaging apparatus, and displays the aligned images on the monitor 928. As illustrated in FIG. 8, the images of the fundus are displayed in order of a surface image S (surface), a tomographic image Ti (luminance information), and the two-dimensional image I (tomogram) on the monitor 928. An acquisition position Li of the two-dimensional image I (tomogram) is overlapped on the two-dimensional image I and the surface image S.

Although 128 tomographic images are generated by the image processing apparatus 100, on the monitor 928, the tomographic image Ti (i=0 to 128) as one selected cross-section or the tomographic image Ti which is a cross-section of a three-dimensionally reconstructed tomographic image (in this case, an arbitrary number i is assigned) is displayed. The operator can switch the displayed tomographic image by operating input units 929-1 and 929-2. Alternatively, the operator can select the tomographic image to be displayed by operating the input units 929-1 and 929-2 to scan and select the location of the displayed two-dimensional image, I with the input units 929-1 and 929-2.

When the tomographic image Ti is switched, the display position of the acquired position Li of the tomographic image Ti displayed on the two-dimensional image I and the surface image S is also updated. Consequently, the operator can easily know where the displayed tomographic image Ti is positioned on the subject's eye fundus 127 because the two-dimensional image I is high in quality.

Further, since the two-dimensional image is high in quality, the tomographic image can be correctly selected by scanning with the input units 929-1 and 929-2.

In addition, since the tomographic image corresponding to the position information on the two-dimensional image I can be directly obtained, there is no deviation in the positional relationship between the retina tomographic image and the intensity image. Consequently, the operator can accurately know the position on the fundus where the tomographic image was captured.

Further, since the two-dimensional image I and the surface image S are aligned, the positional relationship between the position on the surface image S and the acquisition position of the retina tomographic image can be known more accurately based on the information about the two-dimensional image I.

In the present exemplary embodiment, although a two-dimensional image of the retina is generated based on a tomographic image of a subject's eye fundus, a two-dimensional image of an anterior segment may also be generated based on a tomographic image of a subject's eye anterior segment. In this case, the generated two-dimensional image is generated as an image that is analogous to an anterior segment planar image captured from the anterior segment of the subject's eye with a CCD camera. Further, the skin or teeth can also be an object of image capturing.

Further, since image calculation is unnecessary, information about a desired range of the retina can be selected in unit of single pixel.

Consequently, a two-dimensional image can be obtained in which the amount of unnecessary information is reduced.

In the generation unit 1200, the pixel value to be selected is determined based on sorting processing. However, the generation unit 1200 can also be configured so that a predetermined layer of the retina, such as a nerve fiber layer (NFL), is selected, the pixel values in that layer are successively sorted, and a maximum value or an intermediate value is selected. Further, a two-dimensional image of the retina is generated from the selected pixel value. In this case, the information that the operator is more interested in obtaining can be narrowed down and selected. In addition, since image calculation is unnecessary, information about a desired range of the retina can be selected in unit of single pixel.

As a result, a two-dimensional image can be obtained in which the amount of unnecessary information is reduced.

The generation unit 1200 can also be configured so that pixel values equal to or smaller than a predetermined value are removed in advance, the pixel values of the remaining retina area are successively sorted, and a maximum value or an intermediate value is selected. Further, a two-dimensional image of the retina is generated from the selected pixel value. In this case, since the low pixel value area is an area in which there are no interference images, information that is not necessary can be prevented from being selected by removing this area.

In this case, the generation unit 1200 performs sorting processing for replacing the pixel values equal to or smaller than a predetermined value with zero. If zero is included in the generated two-dimensional image, the generation unit 1200 displays a message on the monitor 928 warning that imaging has failed. With this display, the operator can easily determine that imaging needs to be performed again.

Next, a second exemplary embodiment according to the present invention will be described with reference to FIGS. 10 and 11.

Figure 10:
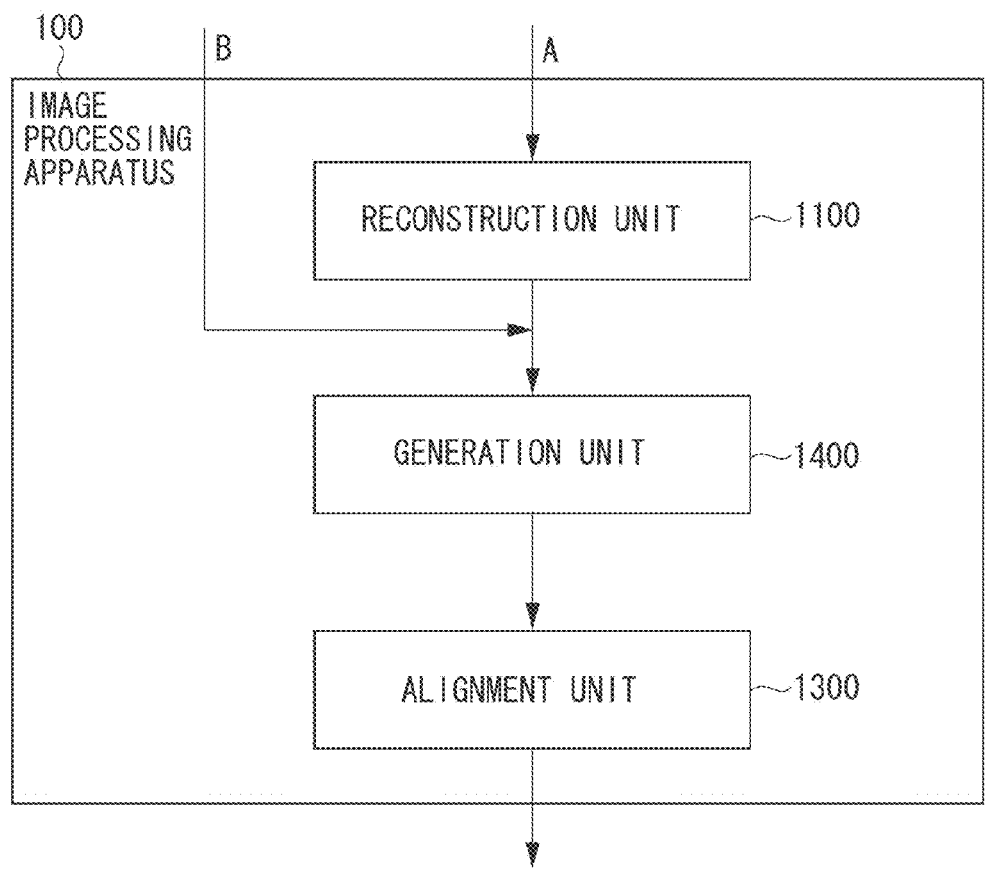
FIG. 10 is a block diagram illustrating a configuration of an image processing apparatus according to a second exemplary embodiment.
Figure 11:
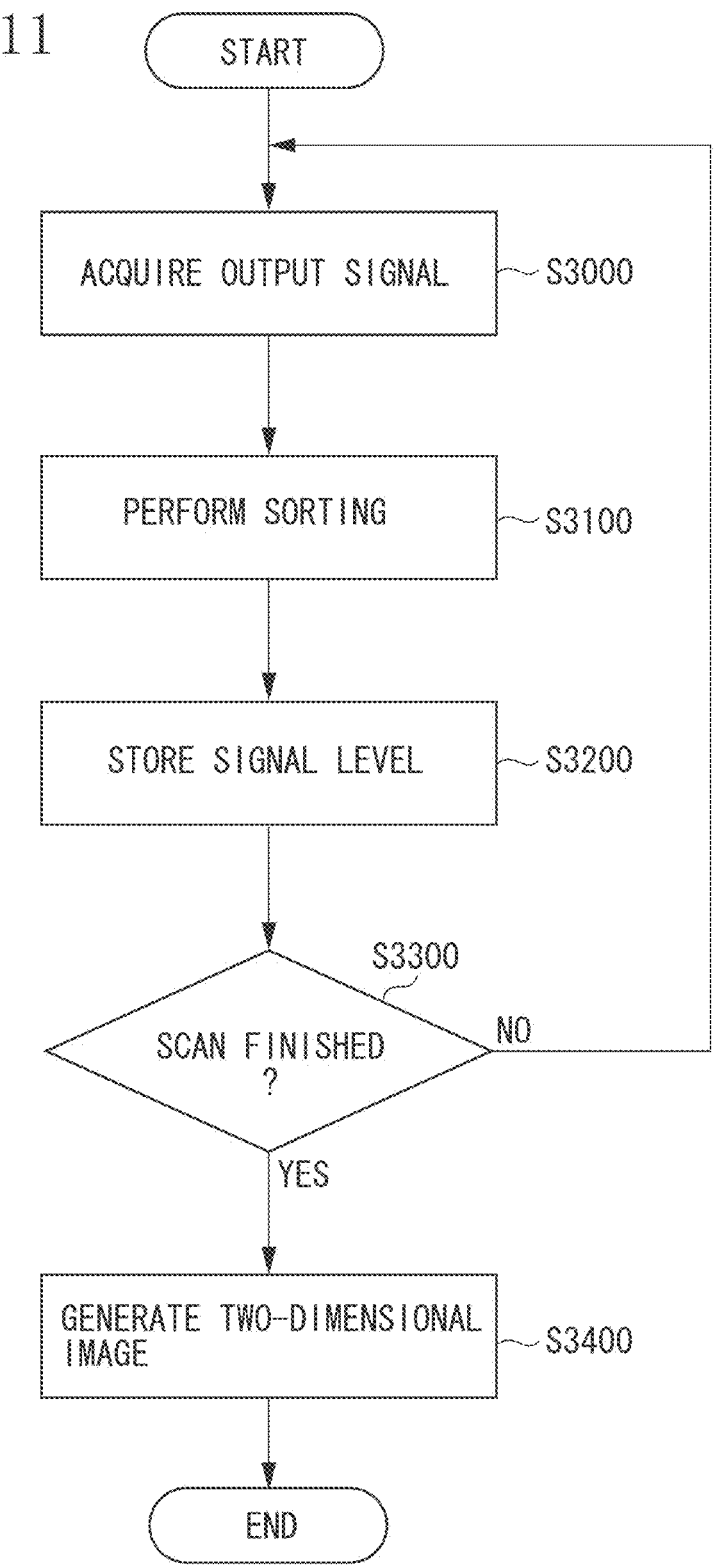
FIG. 11 is a flowchart illustrating a flow of processing performed by an image processing apparatus according to the second exemplary embodiment.

The configuration of the generation unit 1400 in FIG. 10 is different from that according to the first exemplary embodiment. However, other parts are denoted with the same reference numerals, and a description thereof will be omitted. The generation unit 1400 has a path for generating a two-dimensional image that does not go through the reconstruction unit 1100.

In addition to a path A that performs similar processing to that of the first exemplary embodiment, the generation unit 1400 includes a path B for directly receiving an output value from each of a plurality of elements of the line sensor 182 other than of an A scan image. Further, a two-dimensional image is generated by selecting an output value from each of the plurality of elements of the line sensor 182 for each illumination position.

A first mode using the path A and a second mode using the path B are selected by a selection unit 1500 (not illustrated). For example, the selection unit 1500 selects the second mode for a confirmation screen immediately after image capture, and selects the first mode when confirming the specific details of an image.

The processing performed when the first mode is selected is the same as that in the first exemplary embodiment. The processing performed when the second mode is selected will be described below based on the processing flow illustrated in FIG. 11.

As described above, the line sensor 182 has 2,048 pixels, and generates 2,048 image signals. In step S3000, the generation unit 1400 acquires these image signals.

Further, the generation unit 1400 obtains a representative intensity signal at one point on the subject's eye fundus by selectively extracting one image signal from among this plurality of image signals.

In step S3100, the generation unit 1400 sorts the plurality of image signals output from the line sensor 182 in order of larger signal level.

In step S3200, the generation unit 1400 selects an image signal of a predetermined ranking in the main memory 11. This image signal of a predetermined ranking is an image signal positioned n places from the top after the image signals were sorted in order of larger signal level.

The generation unit 1400 determines the signal level of the image signal with the predetermined ranking as the intensity information for that A scan.

The processing from step 3000 to step S3300 is repeated until all A scans are finished. With this operation, intensity information for each different point (corresponding to the A scans) of the fundus 127 can be obtained. In step S3400, a two-dimensional image of the retina as illustrated in FIG. 7 can be obtained by forming this intensity information as a two-dimensional image. If the second mode is selected, the processing can be performed faster than if the first mode is selected.

The output from the line sensor 182 can be performed by performing analog-to-digital (A/D) conversion with the line sensor 182, or by performing A/D conversion with a reception unit in the image processing apparatus 100.

If the present exemplary embodiment is performed employing swept source (SS)-OCT, which changes the light source wavelength, a single light-receiving sensor can be employed instead of the line sensor 182.

In this case, the interference signal is output from the single light-receiving sensor for each scanning position on the fundus as 2,048 image signals that have been subjected to A/D conversion by time-division. These 2,048 image signals are acquired by the generation unit 1400, and then the same processing as that from step S3100 and subsequent steps is performed. With this operation, a two-dimensional image can be rapidly obtained even for SS-OCT. The output from the light-receiving sensor can be subjected to A/D conversion with the light-receiving sensor, or to A/D conversion with the reception unit in the image processing apparatus 100.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190002 filed Aug. 30, 2012, which is hereby incorporated by reference herein in its entirety.

What is claimed is:

1. An imaging apparatus comprising:
   an optical system configured to provide reference light and measurement light;
   a scanning unit configured to scan a fundus of an eye with the measurement light;
   one or more processors; and
   one or more memories coupled to the one or more processors and storing instructions which, when executed by the one or more processors, cause the one or more processors to perform operations comprising:
   acquiring tomographic images of a region of the fundus based on interference light produced by interference between return light reflected by the fundus when irradiated with the measurement light and the reference light, wherein each tomographic image includes rows, each row corresponds to an image of the fundus in a depth direction of the fundus, and each row includes luminance values based on the interference light; and
   generating a two-dimensional image having a plurality of pixels by determining a luminance value of each pixel of the plurality of pixels to be a luminance value equal to a predetermined percentage below the highest luminance value in a ranking from the brightest to the darkest of the luminance values in a corresponding row of a corresponding tomographic image, wherein the predetermined percentage is variable.

2. The imaging apparatus according to claim 1, further comprising a sensor having a plurality of elements configured to convert the interference light received via a diffraction grating into image signals,
   wherein the one or more processors includes a first mode configured to generate the two-dimensional image based on one image signal among image signals of the plurality of elements for each illumination position of the measurement light, and a second mode configured to generate the two-dimensional image based on the ranking of the luminance values in respective pixel rows of the tomographic image.

3. The imaging apparatus according to claim 1, wherein the luminance value equal to the predetermined percentage below the highest luminance value of the luminance values is included in a top half of the ranking.

4. The imaging apparatus according to claim 1, wherein the scanning unit is configured to scan the fundus with the measurement light in at least two directions, and
   the one or more processors is configured to generate the two-dimensional image corresponding to an area of the fundus irradiated with the measurement light via the scanning unit.

5. The imaging apparatus according to claim 1, wherein the one or more processors is configured to generate images in the depth direction of a plurality of different positions of the fundus while scanning with the scanning unit, and generate the tomographic images based on the generated plurality of images in the depth direction.

6. The imaging apparatus according to claim 1, further comprising a display unit configured to display the two-dimensional image generated by the one or more processors.

7. The imaging apparatus according to claim 6, further comprising an imaging unit configured to capture a surface image of the fundus,
   wherein the display unit is configured to display the two-dimensional image and the surface image side-by-side.

8. The imaging apparatus according to claim 6, wherein the display unit is configured to display at least one tomographic image generated by the one or more processors side-by-side with the two-dimensional image.

9. The imaging apparatus according to claim 8, wherein the display unit is configured to display an acquisition position of at least one tomographic image superimposed on the two-dimensional image.

10. The imaging apparatus according to claim 1, wherein the luminance value of the each pixel is determined to be a luminance value in the top half of the ranking from the brightest to the darkest of the luminance values in a predetermined range of the corresponding row of the corresponding tomographic image.

11. The imaging apparatus according to claim 1, wherein the predetermined percentage is 0%, 10%, or 50%.

12. The imaging apparatus according to claim 1, wherein in a case where a layer indicating a range in the depth direction for generating the two-dimensional image is selected the predetermined percentage is different from the predetermined percentage in a case where the layer is not selected.

13. An image processing apparatus comprising:
   one or more processors; and one or more memories coupled to the one or more processors and storing instructions, the instructions, when executed by the one or more processors, cause the one or more processors to perform operations comprising:

acquiring tomographic images in a region of a fundus of an eye based on interference light produced by interference between reference light and return light reflected by the fundus when irradiated with measurement light, wherein each tomographic image includes rows, each row corresponds to an image of the fundus in a depth direction of the fundus, and each row includes luminance values based on the interference light; and generating a two-dimensional image having a plurality of pixels by determining a luminance value of each pixel of the plurality of pixels to be a luminance value equal to a predetermined percentage below the highest luminance value in in a top half of a ranking from the brightest to the darkest of the luminance values in a corresponding row of a corresponding tomographic image, wherein the predetermined percentage is variable.

14. The image processing apparatus according to claim 13, wherein the luminance value of the each pixel is determined to be a luminance value in the top half of the ranking from the brightest to the darkest of the luminance values in a selected layer of the corresponding row of the corresponding tomographic image.

15. The image processing apparatus according to claim 13, wherein the luminance value equal to the predetermined percentage below the highest luminance value of the luminance values is included in a top half of the ranking.

16. The image processing apparatus according to claim 15, wherein the predetermined percentage is 0%, 10% or 50%.

17. The image processing apparatus according to claim 13, wherein the luminance value equal to the predetermined percentage below the highest luminance value is included in a top half of the ranking from the brightest to the darkest of the luminance values in a predetermined range of the corresponding row of the corresponding tomographic image.

18. The image processing apparatus according to claim 13, wherein in a case where a layer indicating a range in the depth direction for generating the two-dimensional image is selected the predetermined percentage is different from the predetermined percentage in a case where the layer is not selected.

19. An image processing method comprising:

acquiring tomographic images in a region of a fundus of an eye based on interference light produced by interference between reference light and return light reflected by the fundus when irradiated with measurement light, wherein each tomographic image includes rows, each row corresponds to an image of the fundus in a depth direction of the fundus, and each row includes luminance values based on the interference light; and generating a two-dimensional image having a plurality of pixels by determining a luminance value of each pixel of the plurality of pixels to be a luminance value equal to a predetermined percentage below the highest luminance value in a ranking from the brightest to the darkest of the luminance values in a corresponding row of a corresponding tomographic image, wherein the predetermined percentage is variable.

20. The image processing method according to claim 19, wherein the luminance value equal to the predetermined percentage below the highest luminance value of the luminance values is included in a top half of the ranking.

21. The image processing method according to claim 20, wherein the luminance value of the each pixel is determined to be a luminance value in the top half of the ranking from the brightest to the darkest of the luminance values in a selected layer of the corresponding row of the corresponding tomographic image.

22. The image processing method according to claim 19, wherein the predetermined percentage is 0%, 10%, or 50%.

23. An image processing method comprising:

acquiring interference light produced by interference between reference light and return light reflected by a fundus of an eye when irradiated with measurement light as a plurality of image signals for each of a plurality of illumination positions of the measurement light, wherein the plurality of image signals corresponds to an image of the fundus in a depth direction of the fundus, and the plurality of image signals includes signal levels based on the interference light; and generating a two-dimensional image having a plurality of pixels by determining a luminance value of each pixel of the plurality of pixels to be a luminance value based on a signal level equal to a predetermined percentage below the largest signal level in a ranking from the largest to the smallest of the signal levels in a corresponding illumination position of the measurement light, wherein the predetermined percentage is variable.

24. The image processing method according to claim 23, wherein the predetermined percentage is 0%, 10%, or 50%.

* * * * *